(12) United States Patent
Van Egmond et al.

(10) Patent No.: US 7,102,048 B2
(45) Date of Patent: Sep. 5, 2006

(54) METHANOL FEED FOR PRODUCING OLEFIN STREAMS

(75) Inventors: Cor F. Van Egmond, Pasadena, TX (US); Teng Xu, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 553 days.

(21) Appl. No.: 10/321,215

(22) Filed: Dec. 17, 2002

(65) Prior Publication Data

US 2004/0116757 A1 Jun. 17, 2004

(51) Int. Cl.
*C07C 1/00* (2006.01)

(52) U.S. Cl. .................. 585/638; 585/324; 585/639; 585/640

(58) Field of Classification Search ............. 585/324, 585/638–640
See application file for complete search history.

(56) References Cited

U.S. PATENT DOCUMENTS

| | | | |
|---|---|---|---|
| 2,321,748 A | 6/1943 | Kopkins et al. | ............... 202/41 |
| 2,506,065 A | 5/1950 | Clark | ............... 260/450 |
| 3,524,819 A | 8/1970 | Guerrieri | |
| 4,013,521 A | 3/1977 | Scott | |
| 4,442,020 A | 4/1984 | Fuderer | |
| 4,520,216 A | 5/1985 | Skov et al. | |
| 4,565,803 A | 1/1986 | Schoenthal et al. | |
| 4,581,157 A | 4/1986 | Twigg | |
| 4,592,806 A | 6/1986 | Ilgner et al. | |
| 4,666,945 A | 5/1987 | Osugi et al. | |
| 4,709,113 A | 11/1987 | Harandi et al. | |
| 4,844,837 A | 7/1989 | Heck et al. | |
| 5,096,470 A | 3/1992 | Krishnamurthy | |
| 5,122,299 A | 6/1992 | LeBlanc | |
| 5,177,114 A | 1/1993 | Van Dijk et al. | |
| 5,254,520 A | 10/1993 | Sofianos | |
| 5,326,550 A | 7/1994 | Adris et al. | |
| 5,368,835 A | 11/1994 | Choudhary et al. | |
| 5,385,949 A | 1/1995 | Tierney et al. | |
| 5,512,599 A | 4/1996 | Hiramatsu et al. | |
| 5,554,351 A | 9/1996 | Primdahl | |
| 5,599,517 A | 2/1997 | Ul-Haque et al. | |
| 5,639,401 A | 6/1997 | Jacobs et al. | |
| 5,648,582 A | 7/1997 | Schmidt et al. | |
| 5,714,662 A | 2/1998 | Vora et al. | |
| 5,856,585 A | 1/1999 | Sanfilippo et al. | |
| 5,998,489 A | 12/1999 | Kobayashi et al. | |
| 6,023,005 A * | 2/2000 | Lattner et al. | ............... 585/639 |
| 6,121,504 A | 9/2000 | Kuechler et al. | ............ 585/640 |
| 6,218,439 B1 | 4/2001 | Kobayashi et al. | |
| 6,258,860 B1 | 7/2001 | Weedon et al. | |
| 6,340,437 B1 | 1/2002 | Yagi et al. | |
| 6,342,538 B1 | 1/2002 | Matsumura et al. | |
| 6,441,262 B1 * | 8/2002 | Fung et al. | ............... 585/640 |
| 6,444,179 B1 | 9/2002 | Sederquist | |
| 6,444,712 B1 | 9/2002 | Janda | |
| 6,458,334 B1 | 10/2002 | Tamhankar et al. | |
| 6,486,218 B1 | 11/2002 | Kobayashi et al. | |
| 6,486,219 B1 | 11/2002 | Janda et al. | |

FOREIGN PATENT DOCUMENTS

DE 28 09 082 11/1978

* cited by examiner

*Primary Examiner*—Walter D. Griffin
*Assistant Examiner*—In Suk Bullock

(57) ABSTRACT

This invention provides a methanol composition, a method of making the composition, and a method of using the composition. The methanol composition of this invention is supplemented with certain additional alcohols and/or aldehydes, and serves as a particularly desirable feed stream for use in the manufacture of olefins such as ethylene and propylene. Such feed streams result in increased production of ethylene or in the increased production of both ethylene and propylene.

134 Claims, No Drawings

METHANOL FEED FOR PRODUCING OLEFIN STREAMS

FIELD OF THE INVENTION

This invention is to a methanol composition, a method of making the composition, and a method of using the composition. More specifically, the methanol composition is particularly suited as a feed for converting oxygenates in the composition to olefins, particularly ethylene and propylene.

BACKGROUND OF THE INVENTION

Methanol is a major chemical raw material used to make a variety of products, including acetic acid, formaldehyde, and methyl tertiary butyl ether. Worldwide demand is expected to significantly increase as new applications for the use of methanol become commercialized. Such new applications include the conversion of methanol to gas, such as the Mobil MTG process; the conversion of methanol to olefins, gasoline and distillate, such as the Mobil MOGD process; and the conversion of methanol to olefins, such as the MTO process.

For example, in U.S. Pat. Nos. 6,444,712 B1 and 6,486,219 B1 to Janda, a method for producing olefins from methanol, by way of using natural gas to make the methanol, is described. The method includes converting the methane component of the natural gas to synthesis gas (syngas) using a steam reformer and a partial oxidation reformer. The syngas from each reformer is combined and sent to a methanol synthesis reactor. The combined syngas stream to the methanol synthesis reactor desirably has a syngas number of from about 1.4 to 2.6. The methanol product is then used as a feed in a methanol to olefin production process.

Much of the methanol made today is made under high purity specifications. Grade A and grade AA methanol are commonly produced. U.S. Pat. No. 4,592,806 to Ignore discloses a process for producing the grade AA methanol. The grade AA methanol has a maximum ethanol content of 10 ppm and is produced using a distillation column, and distilling fusel oil at a reflux ratio of at least 5:1.

The use of crude, or substantially unrefined, methanol has been suggested for use in making olefins. In U.S. Pat. No. 5,714,662 to Vora, there is disclosed an integrated process for producing light olefins from a hydrocarbon gas stream by combining reforming, methanol production, and methanol conversion. The methanol produced is a crude methanol, which is essentially unrefined and comprises methanol, light ends, heavier alcohols. The crude methanol is passed directly to an oxygenate conversion zone to produce light olefins.

As the production of methanol continues to increase, and the new commercial uses of methanol also continue to increase, it would be advantageous to produce methanol streams which have particular advantages for specific end uses. It would be particularly beneficial to produce methanol compositions that provide a greater quantity of end product and/or a better quality of end product for the specific end use.

SUMMARY OF THE INVENTION

This invention provides a methanol composition that is particularly suited as a feed for converting oxygenates in the composition to olefins. The methanol composition is particularly suited for producing high concentrations of ethylene and propylene in the catalytic conversion of oxygenates to olefins using a molecular sieve catalyst. Further provided are methods for making and using the methanol composition.

The methanol composition is ideally provided in large scale quantities (e.g., quantities of at least 10,000 gallons) for conversion to a variety of derivative products. An example of one derivate product includes olefins, which is of great advantage for further conversion of the olefins to polyolefins such as polyethylene and polypropylene. In one embodiment, the methanol composition is transported to a location geographically distinct from that where it was manufactured. Preferably, the methanol composition of this invention is loaded onto a vessel, and the vessel is transported over a body of water to a storage facility or directly to a conversion unit.

In another embodiment, the methanol composition comprises at least 50 wt % methanol, based on total weight of the methanol composition. Preferably, the methanol includes less than 99.85 wt % methanol, based on total weight of the methanol composition.

In yet another embodiment, the methanol composition comprises greater than 10 wppm alcohol supplement, based on total weight of the methanol composition. Preferably, the composition comprises greater than 10 wppm aldehyde supplement, based on total weight of the methanol composition. More preferably, the methanol composition comprises not greater than 12 wt % water, based on total weight of the methanol composition.

In other embodiments, the methanol composition comprises at least 75 wt %, 80 wt %, 85 wt %, or 90 wt % methanol, based on total weight of the methanol composition. In yet other embodiments the methanol composition comprises not greater than 99 wt %, 98 wt %, 97 wt %, or 96 wt % methanol, based on total weight of the methanol composition.

The methanol composition optionally comprises at least 100 wppm, 1,000 wppm, 10,000, or 0.1 wt % alcohol supplement, based on total weight of the methanol composition. Alternatively, the methanol composition comprises not greater than 15 wt %, 12 wt %, 10 wt %, or not greater than 8 wt % alcohol supplement, based on total weight of the methanol composition.

Optionally, methanol composition comprises at least 100 wppm, 1,000 wppm, 10,000 wppm, or 0.1 wt % aldehyde supplement, based on total weight of the methanol composition. Alternatively, the methanol composition comprises not greater than 15 wt %, 12 wt %, 10 wt %, or 8 wt % aldehyde supplement, based on total weight of the methanol composition.

In one embodiment, the alcohol supplement is at least one alcohol selected from the group consisting of ethanol, propanol and butanol. Preferably, the alcohol supplement is ethanol.

In another embodiment, the aldehyde supplement is at least one aldehyde selected from the group consisting of formaldehyde, acetaldehyde, proprionaldehyde, butyraldehyde, and valeraldehyde. Preferably, the aldehyde supplement is acetaldehyde.

In another optional embodiment, the methanol composition further comprises ketone at less than 50%, 60%, or 70% of that of the alcohol supplement or the aldehyde supplement. Alternatively, the methanol composition further comprises at least 0.1 wt % water, 0.5 wt %, 1.0, or 1.5 wt % water, based on total weight of the methanol composition. Preferably, the methanol composition further comprises not greater than 10 wt %, 8 wt %, or 5 wt % water, based on total weight of the methanol composition.

There is further provided a process for forming an olefin stream. In one embodiment, the process comprises contacting a synthesis gas stream with a methanol synthesis catalyst to form a crude methanol stream containing methanol, ethanol and acetaldehyde. A methanol composition is separated from the crude methanol stream, wherein the methanol composition comprises a majority of the methanol and a majority of the acetaldehyde or ethanol contained in the oxygenate containing stream. The methanol composition is then contacted with an olefin forming catalyst to form an olefin stream.

In another embodiment, there is provided a crude methanol stream from which a methanol composition is separated. Preferably, the methanol composition is the composition of this invention, and the composition can be used for a variety of uses, particularly as a feedstock in an oxygenate to olefins conversion process to produce an olefin stream.

A variety of hydrocarbons can be used to form the methanol composition of this invention. Examples of such hydrocarbons include biomass, natural gas, $C_1$ to $C_5$ hydrocarbons, naphtha, heavy petroleum coils, coke, and mixtures thereof. A methane containing gas is a preferred hydrocarbon to use in making the methanol composition of this invention.

In one embodiment, the hydrocarbon feedstock is converted to synthesis gas, then the synthesis gas is converted to crude methanol. The methanol composition is then separated from the crude methanol.

In another embodiment of the invention, a synthesis gas stream is contacted with a methanol synthesis catalyst to form a crude methanol stream. The crude methanol stream contains, in addition to methanol, a variety of hydrocarbon compounds. As one example, the crude methanol stream contains methanol, ethanol and/or acetaldehyde. The methanol composition of the invention is, preferably, recovered from the crude methanol stream.

DETAILED DESCRIPTION OF THE INVENTION

I. Introduction

This invention is directed to a methanol composition, a method for making the methanol composition, and a method of using the methanol composition. The methanol composition is a robust composition that is suitable for contacting with an olefin forming catalyst to form an olefin stream. It can be made from various carbon materials at a relatively large scale for commercial scale processing and upgrading. Because the methanol composition is fairly robust and can be made at such relatively large scales, it can also be transported to geographically distinct locations which are fairly remote from the site of manufacture for use as a feed stock.

The methanol composition of this invention is supplemented with certain additional alcohols and/or aldehydes, and serves as a particularly desirable feed stream for use in the manufacture of olefins such as ethylene and propylene. Such feed streams result in increased production of ethylene or in the increased production of both ethylene and propylene. The methanol stream is particularly suitable for use as a feed stream in a catalytic process, which uses an olefin forming catalyst to convert the oxygenate components in the methanol steam to ethylene and propylene. The ethylene and propylene are then recovered and used for further processing, such as in the manufacture of polyethylene and polypropylene.

II. Description of the Methanol Composition

The methanol composition of this invention contains less than 99.85 wt % methanol, based on total weight of the composition, and is supplemented with other oxygenates, such as alcohols and/or aldehydes, which are particularly suited for use as a feed component in the catalytic conversion of the oxygenates to olefins. In one embodiment of the invention, the methanol composition comprises at least about 50 wt % methanol, based on total weight of the composition. Desirably, the methanol composition comprises at least about 75 wt % methanol, preferably at least about 80 wt % methanol, more preferably at least about 85 wt % methanol, and most preferably at least about 90 wt % methanol, based on total weight of the composition.

In another embodiment of the invention, the methanol composition comprises not greater than 99 wt % methanol, based on total weight of the composition. Preferably, the methanol composition comprises not greater than 98 wt % methanol, more preferably not greater than 97 wt % methanol, and most preferably not greater than 96 wt % methanol, based on total weight of the composition.

In this invention, the methanol composition is supplemented with other alcohols and/or aldehydes that are particularly effective the manufacture of olefins, particularly ethylene and/or propylene. Such alcohol and aldehyde supplements include those that have a boiling point not lower than that of formaldehyde, but preferably not higher than that of butanol.

Examples of alcohol compounds, which are useful in the methanol composition of this invention, besides methanol, include ethanol, propanol and butanol. Ethanol and propanol are preferred, and ethanol is particularly preferred.

In one embodiment of the invention, the methanol composition comprises greater than 10 wppm alcohol supplement, based on total weight of the composition, the alcohol supplement being an alcohol having a boiling point not lower than that of formaldehyde, but not higher than that of butanol. Desirably, the methanol composition comprises at least about 100 wppm alcohol supplement. Preferably, the methanol composition comprises at least about 1,000 wppm alcohol supplement, more preferably at least about 10,000 wppm alcohol supplement, and most preferably at least about 0.1 wt % alcohol supplement, based on total weight of the composition. Preferably, the alcohol supplement is at least one alcohol selected from the group consisting of ethanol, propanol and butanol.

In another embodiment of the invention, the methanol composition comprises not greater than 15 wt % of the alcohol supplement, based on total weight of the composition. Preferably, the methanol composition comprises not greater than 12 wt % of the alcohol supplement, more preferably not greater than 10 wt % of the alcohol supplement, and most preferably not greater than 8 wt % of the alcohol supplement, based on total weight of the composition.

Examples of aldehyde compounds which are useful in the methanol composition of this invention include, besides formaldehyde, acetaldehyde, proprionaldehyde, butyraldehyde, and valeraldehyde. Preferred aldehydes include acetaldehyde and proprionaldehyde. Particularly preferred is acetaldehyde.

In one embodiment of the invention, the methanol composition comprises greater than 10 wppm aldehyde supplement, the aldehyde supplement being an aldehyde a boiling point at least as high as that of formaldehyde, but not higher than that of butanol. Desirably, the methanol composition comprises at least about 100 wppm aldehyde supplement.

Preferably, the methanol composition comprises at least about 1,000 wppm aldehyde supplement, more preferably at least about 10,000 wppm aldehyde supplement, and most preferably at least about 0.1 wt % aldehyde supplement, based on total weight of the composition. Preferably, the natural aldehyde supplement is at least one aldehyde selected from the group consisting of formaldehyde, acetaldehyde, proprionaldehyde, butyraldehyde, and valeraldehyde.

In another embodiment of the invention, the methanol composition comprises not greater than 15 wt % of the aldehyde supplement, based on total weight of the composition. Preferably, the methanol composition comprises not greater than 12 wt % of the aldehyde supplement, more preferably not greater than 10 wt % of the aldehyde supplement, and most preferably not greater than 8 wt % of the aldehyde supplement, based on total weight of the composition.

Although the methanol composition of this invention can include other components, the other components are included in a concentration such that the methanol composition remains suitable for contacting with an olefin forming catalyst to form an olefin stream. In one embodiment, the methanol-composition further includes ketones, but in a concentration less than that of the alcohol supplement or the aldehyde supplement. Preferably the ketone concentration will be less than 50% that of the alcohol supplement or the aldehyde supplement, more preferably less than 60% of the alcohol supplement or the aldehyde supplement, and most preferably less than 70% of the alcohol supplement or the aldehyde supplement. Examples of such ketones include one or more of acetone, methyl ethyl ketone, and any one or more of the pentanones. Preferably, the methanol composition includes not greater than 1 wt % ketones, more preferably not greater than 0.1 wt % ketones, and most preferably not greater than 0.0 1 wt % ketones, based on total weight of the composition.

In another embodiment of the invention, the methanol composition includes ketones at a minimum concentration of 100 wppm, based on total weight of the composition. Preferably, the minimum concentration of ketones in the composition is 10 wppm, more preferably 1 wppm, and most preferably 0.01 wppm, based on total weight of the composition.

In another embodiment, the methanol composition includes water. The water content should not be so high that shipping costs are prohibitive, but of sufficient quantity to exert a positive partial pressure in the methanol to olefin conversion reaction, thereby increasing selectivity to ethylene and/or propylene. Desirably, the water content is at least about 0.1 wt %, based on total weight of the methanol composition. Preferably, the methanol composition contains at least about 0.5 wt % water, more preferably at least about 1.0 wt % water, and most preferably at least about 1.5 wt % water, based on total weight of the methanol composition.

In another embodiment, the methanol composition contains not greater than about 12 wt % water, based on total weight of the methanol composition. Preferably, the methanol composition contains not greater than about 10 wt % water, more preferably not greater than about 8 wt % water, and most preferably not greater than about 5 wt % water, based on total weight of the methanol composition.

III. Method of Making the Methanal Composition

A. Examples of Methanol Synthesis Processes

The methanol composition of this invention can be manufactured from a variety of carbon sources. Examples of such sources include biomass, natural gas, $C_1$–$C_5$ hydrocarbons, naphtha, heavy petroleum oils, or coke (i.e., coal). Preferably, the hydrocarbon feed stream comprises methane in an amount of at least about 50% by volume, more preferably at least about 70% by volume, most preferably at least about 80% by volume. In one embodiment of this invention natural gas is the preferred hydrocarbon feed source.

One way of converting the carbon source to a methanol composition is to first convert the carbon source to synthesis gas (syngas), and then converting the syngas to the methanol composition. Any conventional process can be used. In particular, any conventional carbon oxide conversion catalyst can be used to convert the syngas to the methanol composition. In one embodiment, the carbon oxide conversion catalyst is a nickel containing catalyst.

Synthesis gas comprises carbon monoxide and hydrogen. Optionally, carbon dioxide and nitrogen are included. Conventional processes for converting carbon components to syngas include steam reforming, partial oxidation, and autothermal reforming.

The hydrocarbon feed stream that is used in the conversion of hydrocarbon to synthesis gas, is optionally treated to remove impurities that can cause problems in further processing of the hydrocarbon feed stream. These impurities can poison many conventional propylene and ethylene forming catalysts. A majority of the impurities, which may be present, can be removed in any conventional manner. The hydrocarbon feed is preferably purified to remove sulfur compounds, nitrogen compounds, particulate matter, other condensables, and/or other potential catalyst poisons prior to being converted into synthesis gas.

In one embodiment of the invention, the hydrocarbon feed stream is passed to a synthesis gas plant. Synthesis gas refers to a combination of hydrogen and carbon oxide produced in a synthesis gas plant from a hydrocarbon feed, the synthesis gas having an appropriate molar ratio of hydrogen to carbon oxide (carbon monoxide and/or carbon dioxide), as described below. The synthesis gas plant may employ any conventional means of producing synthesis gas, including partial oxidation, steam or $CO_2$ reforming, or some combination of these two chemistries.

Steam reforming generally comprises contacting a hydrocarbon with steam to form synthesis gas. The process preferably includes the use of a catalyst.

Partial oxidation generally comprises contacting a hydrocarbon with oxygen or an oxygen containing gas such as air to form synthesis gas. Partial oxidation takes place with or without the use of a catalyst, although the use of a catalyst is preferred. In one embodiment, water (steam) is added with the feed in the partial oxidation process. Such an embodiment is generally referred to as autothermal reforming.

Conventional synthesis gas-generating processes include gas phase partial oxidation, autothermal reforming, fluid bed synthesis gas generation, catalytic partial oxidation and various processes for steam reforming.

B. Steam Reforming to Make Syngas

In the catalytic steam reforming process, hydrocarbon feeds are converted to a mixture of $H_2$, CO and $CO_2$ by reacting hydrocarbons with steam over a catalyst. This process involves the following reactions:

$$CH_4 + H_2O \leftrightharpoons CO + 3H \quad (1)$$

or $$C_nH_m + nH_2O \leftrightharpoons nCO + [n+(m/2)]H_2 \quad (2)$$

and $$CO + H_2O \leftrightharpoons CO_2 + H2 \quad (3) \text{ (shift reaction)}$$

The reaction is carried out in the presence of a catalyst. Any conventional reforming type catalyst can be used. The catalyst used in the step of catalytic steam reforming comprises at least one active metal or metal oxide of Group 6 or Group 8–10 of the Periodic Table of the Elements. The Periodic Table of the Elements referred to herein is that from *CRC Handbook of Chemistry and Physics*, 82$^{nd}$ Edition, 2001–2002, CRC Press LLC, which is incorporated herein by reference.

In one embodiment, the catalyst contains at least one Group 6 or Group 8–10 metal, or oxide thereof, having an atomic number of 28 or greater. Specific examples of reforming catalysts that can be used are nickel, nickel oxide, cobalt oxide, chromia and molybdenum oxide. Optionally, the catalyst is employed with least one promoter. Examples of promoters include alkali and rare earth promoters. Generally, promoted nickel oxide catalysts are preferred.

The amount of Group 6 or Group 8–10 metals in the catalyst can vary. Preferably, the catalyst includes from about 3 wt % to about 40 wt % of at least one Group 6 or Group 8–10 metal, based on total weight of the catalyst. Preferably, the catalyst includes from about 5 wt % to about 25 wt % of at least one Group 6 or Group 8–10 metal, based on total weight of the catalyst.

The reforming catalyst optionally contains one or more metals to suppress carbon deposition during steam reforming. Such metals are selected from the metals of Group 14 and Group 15 of the Periodic Table of the Elements. Preferred Group 14 and Group 15 metals include germanium, tin, lead, arsenic, antimony, and bismuth. Such metals are preferably included in the catalyst in an amount of from about 0.1 wt % to about 30 wt %, based on total weight of nickel in the catalyst.

In a catalyst comprising nickel and/or cobalt there may also be present one or more platinum group metals, which are capable of increasing the activity of the nickel and/or cobalt and of decreasing the tendency to carbon lay-down when reacting steam with hydrocarbons higher than methane. The concentration of such platinum group metal is typically in the range 0.0005 to 0.1% as metal, calculated as the whole catalyst unit. Further, the catalyst, especially in preferred forms, can contain a platinum group metal but no non-noble catalytic component. Such a catalyst is more suitable for the hydrocarbon steam reforming reaction than one containing a platinum group metal on a conventional support because a greater fraction of the active metal is accessible to the reacting gas. A typical content of platinum group metal when used alone is in the range 0.0005 to 0.5% w/w as metal, calculated on the whole catalytic unit.

In one embodiment, the reformer unit includes tubes which are packed with solid catalyst granules. Preferably, the solid catalyst granules comprise nickel or other catalytic agents deposited on a suitable inert carrier material. More preferably, the catalyst is NiO supported on calcium aluminate, alumina, spinel type magnesium aluminum oxide or calcium aluminate titanate.

In yet another embodiment, both the hydrocarbon feed stream and the steam are preheated prior to entering the reformer. The hydrocarbon feedstock is preheated up to as high a temperature as is consistent with the avoiding of undesired pyrolysis or other heat deterioration. Since steam reforming is endothermic in nature, and since there are practical limits to the amount of heat that can be added by indirect heating in the reforming zones, preheating of the feed is desired to facilitate the attainment and maintenance of a suitable temperature within the reformer itself. Accordingly, it is desirable to preheat both the hydrocarbon feed and the steam to a temperature of at least 200° C.; preferably at least 400° C. The reforming reaction is generally carried out at a reformer temperature of from about 500° C. to about 1,200° C., preferably from about 800° C. to about 1,100° C., and more preferably from about 900° C. to about 1,050° C.

Gas hourly space velocity in the reformer should be sufficient for providing the desired CO to $CO_2$ balance in the synthesis gas. Preferably, the gas hourly space velocity (based on wet feed) is from about 3,000 per hour to about 10,000 per hour, more preferably from about 4,000 per hour to about 9,000 per hour, and most preferably from about 5,000 per hour to about 8,000 per hour.

Any conventional reformer can be used in the step of catalytic steam reforming. The use of a tubular reformer is preferred. Preferably, the hydrocarbon feed is passed to a tubular reformer together with steam, and the hydrocarbon and steam contact a steam reforming catalyst. In one embodiment, the steam reforming catalyst is disposed in a plurality of furnace tubes that are maintained at an elevated temperature by radiant heat transfer and/or by contact with combustion gases. Fuel, such as a portion of the hydrocarbon feed, is burned in the reformer furnace to externally heat the reformer tubes therein. See, for example, Kirk-Othmer, *Encyclopedia of Chemical Technology*, 3rd Ed., 1990, vol. 12, p. 951; and *Ullmann's Encyclopedia of Industrial Chemistry*, 5th Ed., 1989, vol. A-12, p. 186, the relevant portions of each being fully incorporated herein by reference.

The ratio of steam to hydrocarbon feed will vary depending on the overall conditions in the reformer. The amount of steam employed is influenced by the requirement of avoiding carbon deposition on the catalyst, and by the acceptable methane content of the effluent at the reforming conditions maintained. On this basis, the mole ratio of steam to hydrocarbon feed in the conventional primary reformer unit is preferably from about 1.5:1 to about 5:1, preferably from about 2:1 to about 4:1.

The hydrogen to carbon oxide ratio of the synthesis gas produced will vary depending on the overall conditions of the reformer. Preferably, the molar ratio of hydrogen to carbon oxide in the synthesis gas will range from about 1:1 to about 5:1. More preferably the molar ratio of hydrogen to carbon oxide will range from about 2:1 to about 3:1. Even more preferably the molar ratio of hydrogen to carbon oxide will range from about 2:1 to about 2.5:1. Most preferably the molar ration of hydrogen to carbon oxide will range from about 2:1 to about 2.3:1.

Steam reforming is generally carried out at superatmospheric pressure. The specific operating pressure employed is influenced by the pressure requirements of the subsequent process in which the reformed gas mixture is to be employed. Although any superatmospheric pressure can be used in practicing the invention, pressures of from about 175 psig (1,308 kPa abs.) to about 1,100 psig (7,686 kPa abs.) are desirable. Preferably, steam reforming is carried out at a pressure of from about 300 psig (2,170 kPa abs.) to about 800 psig (5,687 kPa abs.), more preferably from about 350 psig (2,515 kPa abs.) to about 700 psig (4,928 kPa abs.).

C. Partial Oxidation to Make Syngas

The invention further provides for the production of synthesis gas, or CO and $H_2$, by oxidative conversion (also referred to herein as partial oxidation) of hydrocarbon, particularly natural gas and $C_1$–$C_5$ hydrocarbons. According to the process, hydrocarbon is reacted with free-oxygen to form the CO and $H_2$. The process is carried out with or without a catalyst. The use of a catalyst is preferred, preferably with the catalyst containing at least one non-transition or transition metal oxides. The process is essentially exothermic, and is an incomplete combustion reaction, having the following general formula:

$$C_nH_m+(n/2)O_2 \rightleftharpoons nCO+(m/2)H_2 \qquad (4)$$

Non-catalytic partial oxidation of hydrocarbons to $H_2$, CO and $CO_2$ is desirably used for producing syngas from heavy fuel oils, primarily in locations where natural gas or lighter hydrocarbons, including naphtha, are unavailable or uneconomical compared to the use of fuel oil or crude oil. The non-catalytic partial oxidation process is carried out by injecting preheated hydrocarbon, oxygen and steam through a burner into a closed combustion chamber. Preferably, the individual components are introduced at a burner where they meet in a diffusion flame, producing oxidation products and heat. In the combustion chamber, partial oxidation of the hydrocarbons generally occurs with less than stoichiometric oxygen at very high temperatures and pressures. Preferably, the components are preheated and pressurized to reduce reaction time. The process preferably occurs at a temperature of from about 1,350° C. to about 1,600° C., and at a pressure of from above atmospheric to about 150 atm.

Catalytic partial oxidation comprises passing a gaseous hydrocarbon mixture, and oxygen, preferably in the form of air, over reduced or unreduced composite catalysts. The reaction is optionally accompanied by the addition of water vapor (steam). When steam is added, the reaction is generally referred to as autothermal reduction. Autothermal reduction is both exothermic and endothermic as a result of adding both oxygen and water.

In the partial oxidation process, the catalyst comprises at least one transition element selected from the group consisting of Ni, Co, Pd, Ru, Rh, Ir, Pt, Os and Fe. Preferably, the catalyst comprises at least one transition element selected from the group consisting of Pd, Pt, and Rh. In another embodiment, preferably the catalyst comprises at least one transition element selected form the group consisting of Ru, Rh, and Ir.

In one embodiment, the partial oxidation catalyst further comprises at least one metal selected from the group consisting of Ti, Zr, Hf, Y, Th, U, Zn, Cd, B, Al, Ti, Si, Sn, Pb, P, Sb, Bi, Mg, Ca, Sr, Ba, Ga, V, and Sc. Also, optionally included in the partial oxidation catalyst is at least one rare earth element selected from the group consisting of La, Ce, Pr, Nd, Pm, Sm, Eu, Gd, Tb, Dy, Ho, Er, Tm, Yb and Lu.

In another embodiment the catalyst employed in the process may comprise a wide range of catalytically active components, for example Pd, Pt, Rh, Ir, Os, Ru, Ni, Cr, Co, Ce, La and mixtures thereof. Materials not normally considered to be catalytically active may also be employed as catalysts, for example refractory oxides such as cordierite, mullite, mullite aluminium titanate, zirconia spinels and alumina.

In yet another embodiment, the catalyst is comprised of metals selected from those having atomic number 21 to 29, 40 to 47 and 72 to 79, the metals Sc, Ti V, Cr, Mn, Fe, Co, Ni, Cu, Zr, Nb, Mo, Tc, Ru, Rh, Pd, Ag, Hf, Ta, W, Re, Os Ir, Pt, and Au. The preferred metals are those in Group 8 of the Periodic Table of the Elements, that is Fe, Os, Co, Re, Ir, Pd, Pt, Ni, and Ru.

In another embodiment, the partial oxidation catalyst comprises at least one transition or non-transition metal deposited on a monolith support. The monolith supports are preferably impregnated with a noble metal such as Pt, Pd or Rh, or other transition metals such as Ni, Co, Cr and the like. Desirably, these monolith supports are prepared from solid refractory or ceramic materials such as alumina, zirconia, magnesia, ceria, silica, titania, mixtures thereof, and the like. Mixed refractory oxides, that is refractory oxides comprising at least two cations, may also be employed as carrier materials for the catalyst.

In one embodiment, the catalyst is retained in form of a fixed arrangement. The fixed arrangement generally comprises a fixed bed of catalyst particles. Alternatively, the fixed arrangement comprises the catalyst in the form of a monolith structure. The fixed arrangement may consist of a single monolith structure or, alternatively, may comprise a number of separate monolith structures combined to form the fixed arrangement. A preferred monolith structure comprises a ceramic foam. Suitable ceramic foams for use in the process are available commercially.

In yet another embodiment, the feed comprises methane, and the feed is injected with oxygen into the partial oxidation reformer at a methane to oxygen (i.e., $O_2$) ratio of from about 1.2:1 to about 10:1. Preferably the feed and oxygen are injected into the reformer at a methane to oxygen ratio of from about 1.6:1 to about 8:1, more preferably from about 1.8:1 to about 4:1.

Water may or may not be added to the partial oxidation process. When added, the concentration of water injected into the reformer is not generally greater than about 65 mole %, based on total hydrocarbon and water feed content. Preferably, when water is added, it is added at a water to methane ratio of not greater than 3:1, preferably not greater than 2:1.

The catalyst may or may not be reduced before the catalytic reaction. In one embodiment, the catalyst is reduced and reduction is carried out by passing a gaseous mixture comprising hydrogen and inert gas (e.g., $N_2$, He, or Ar) over the catalyst in a fixed bed reactor at a catalyst reduction pressure of from about 1 atm to about 5 atm, and a catalyst reduction temperature of from about 300° C. to about 700° C. Hydrogen gas is used as a reduction gas, preferably at a concentration of from about 1 mole % to about 100 mole %, based on total amount of reduction gas. Desirably, the reduction is further carried out at a space velocity of reducing gas mixture of from about $10^3$ cm$^3$/g·hr to about $10^5$ cm$^3$/g·hr for a period of from about 0.5 hour to about 20 hours.

In one embodiment, the partial oxidation catalyst is not reduced by hydrogen. When the catalyst is not reduced by hydrogen before the catalytic reaction, the reduction of the catalyst can be effected by passing the hydrocarbon feed and oxygen (or air) over the catalyst at temperature in the range of from about 500° C. to about 900° C. for a period of from about 0.1 hour to about 10 hours.

In the partial oxidation process, carbon monoxide (CO) and hydrogen ($H_2$) are formed as major products, and water and carbon dioxide ($CO_2$) as minor products. The gaseous product stream comprises the above mentioned products, unconverted reactants (i.e. methane or natural gas and oxygen) and components of feed other than reactants.

When water is added in the feed, the $H_2$:CO mole ratio in the product is increased by the shift reaction: $CO+H_2O \rightleftharpoons H_2+CO_2$. This reaction occurs simultaneously with the oxidative conversion of the hydrocarbon in the feed to CO and $H_2$ or synthesis gas. The hydrocarbon used as feed in the partial oxidation process is preferably in the gaseous phase when contacting the catalyst. The partial oxidation process is particularly suitable for the partial oxidation of methane, natural gas, associated gas or other sources of light hydrocarbons. In this respect, the term "light hydrocarbons" is a reference to hydrocarbons having from 1 to 5 carbon atoms. The process may be advantageously applied in the conversion of gas from naturally occurring reserves of methane which contain substantial amounts of carbon dioxide. In one embodiment, the hydrocarbon feed preferably contains from about 10 mole % to about 90 mole % methane, based on total feed content. More preferably, the hydrocarbon feed contains from about 20 mole % to about 80 mole % methane, based on total feed content. In another embodiment, the feed comprises methane in an amount of at least 50% by volume, more preferably at least 70% by volume, and most preferably at least 80% by volume.

In one embodiment of the invention, the hydrocarbon feedstock is contacted with the catalyst in a mixture with an oxygen-containing gas. Air is suitable for use as the oxygen-containing gas. Substantially pure oxygen as the oxygen-containing gas is preferred on occasions where there is a need to avoid handling large amounts of inert gas such as nitrogen. The feed optionally comprises steam.

In another embodiment of the invention, the hydrocarbon feedstock and the oxygen-containing gas are preferably present in the feed in such amounts as to give an oxygen-to-carbon ratio in the range of from about 0.3:1 to about 0.8:1, more preferably, in the range of from about 0.45:1 to about 0.75:1. References herein to the oxygen-to-carbon ratio refer to the ratio of oxygen in the from of oxygen molecules ($O_2$) to carbon atoms present in the hydrocarbon feedstock. Preferably, the oxygen-to-carbon ratio is in the range of from about 0.45:1 to about 0.65: 1, with oxygen-to-carbon ratios in the region of the stoichiometric ratio of 0.5:1, that is ratios in the range of from about 0.45:1 to about 0.65:1, being more preferred. When steam is present in the feed, the steam-to-carbon ratio is not greater than about 3.0:1, more preferably not greater than about 2.0:1. The hydrocarbon feedstock, the oxygen-containing gas and steam, if present, are preferably well mixed prior to being contacted with the catalyst.

The partial oxidation process is operable over a wide range of pressures. For applications on a commercial scale, elevated pressures, that is pressures significantly above atmospheric pressure, are preferred. In one embodiment, the partial oxidation process is operated at pressures of greater than atmospheric up to about 150 bars. Preferably, the partial oxidation process is operated at a pressure in the range of from about 2 bars to about 125 bars, more preferably from about 5 bars to about 100 bars.

The partial oxidation process is also operable over a wide range of temperatures. At commercial scale, the feed is preferably contacted with the catalyst at high temperatures. In one embodiment, the feed mixture is contacted with the catalyst at a temperature in excess of 600° C. Preferably, the feed mixture is contacted with the catalyst at a temperature in the range of from about 600° C. to about 1,700° C., more preferably from about 800° C. to about 1,600° C. The feed mixture is preferably preheated prior to contacting the catalyst.

The feed is provided during the operation of the process at a suitable space velocity to form a substantial amount of CO in the product. In one embodiment, gas space velocities (expressed in normal liters of gas per kilogram of catalyst per hour) are in the range of from about 20,000 Nl/kg/hr to about 100,000,000 Nl/kg/hr, more preferably in the range of from about 50,000 Nl/kg/hr to about 50,000,000 Nl/kg/hr, and most preferably in the range of from about 500,000 Nl/kg/hr to about 30,000,000 Nl/kg/hr.

D. Combination Syngas Processes

Combination reforming processes can also be incorporated into this invention. Examples of combination reforming processes include autothermal reforming and fixed bed syngas generation. These processes involve a combination of gas phase partial oxidation and steam reforming chemistry.

The autothermal reforming process preferably comprises two synthesis gas generating processes, a primary oxidation process and a secondary steam reforming process. In one embodiment, a hydrocarbon feed stream is steam reformed in a tubular primary reformer by contacting the hydrocarbon and steam with a reforming catalyst to form a hydrogen and carbon monoxide containing primary reformed gas, the carbon monoxide content of which is further increased in the secondary reformer. In one embodiment, the secondary reformer includes a cylindrical refractory lined vessel with a gas mixer, preferably in the form of a burner in the inlet portion of the vessel and a bed of nickel catalyst in the lower portion. In a more preferred embodiment, the exit gas from the primary reformer is mixed with air and residual hydrocarbons, and the mixed gas partial oxidized to carbon monoxides.

In another embodiment incorporating the autothermal reforming process, partial oxidation is carried out as the primary oxidating process. Preferably, hydrocarbon feed, oxygen, and optionally steam, are heated and mixed at an outlet of a single large coaxial burner or injector which discharges into a gas phase partial oxidation zone. Oxygen is preferably supplied in an amount which is less than the amount required for complete combustion.

Upon reaction in the partial oxidation combustion zone, the gases flow from the primary reforming process into the secondary reforming process. In one embodiment, the gases are passed over a bed of steam reforming catalyst particles or a monolithic body, to complete steam reforming. Desirably, the entire hydrocarbon conversion is completed by a single reactor aided by internal combustion.

In an alternative embodiment of the invention, a fixed bed syngas generation process is used to form synthesis gas. In the fixed bed syngas generation process, hydrocarbon feed and oxygen or an oxygen-containing gas are introduced separately into a fluid catalyst bed. Preferably, the catalyst is comprised of nickel and supported primarily on alpha alumina.

The fixed bed syngas generation process is carried out at conditions of elevated temperatures and pressures that favor the formation of hydrogen and carbon monoxide when, for example, methane is reacted with oxygen and steam. Preferably, temperatures are in excess of about 1,700° F. (927° C.), but not so high as to cause disintegration of the catalyst or the sticking of catalyst particles together. Preferably, temperatures range from about 1,750° F. (954° C.) to about 1,950° F. (1,066° C.), more preferably, from about 1,800° F. (982° C.) to about 1,850° F. (1,010° C.).

Pressure in the fixed bed syngas generation process may range from atmospheric to about 40 atmospheres. In one embodiment, pressures of from about 20 atmospheres to about 30 atmospheres are preferred, which allows subsequent processes to proceed without intermediate compression of product gases.

In one embodiment of the invention, methane, steam, and oxygen are introduced into a fluid bed by separately injecting the methane and oxygen into the bed. Alternatively, each stream is diluted with steam as it enters the bed. Preferably, methane and steam are mixed at a methane to steam molar ratio of from about 1:1 to about 3:1, and more preferably from about 1.5:1 to about 2.5:1, and the methane and steam mixture is injected into the bed. Preferably, the molar ratio of oxygen to methane is from about 0.2:1 to about 1.0:1, more preferably from about 0.4:1 to about 0.6:1.

In another embodiment of the invention, the fluid bed process is used with a nickel based catalyst supported on alpha alumina. In another embodiment, silica is included in the support. The support is preferably comprised of at least 95 wt % alpha alumina, more preferably at least about 98% alpha alumina, based on total weight of the support.

In one embodiment, a gaseous mixture of hydrocarbon feedstock and oxygen-containing gas are contacted with a reforming catalyst under adiabatic conditions. For the purposes of this invention, the term "adiabatic" refers to reaction conditions in which substantially all heat loss and radiation from the reaction zone are prevented, with the exception of heat leaving in the gaseous effluent stream of the reactor.

E. Converting Syngas to Methanol

The synthesis gas is sent to a methanol synthesis process and converted to a methanol composition. The methanol synthesis gas process is accomplished in the presence of a methanol synthesis catalyst.

In one embodiment, the synthesis gas is sent as is to the methanol synthesis process. In another embodiment, the hydrogen, carbon monoxide, and/or carbon dioxide content of the synthesis gas is adjusted for efficiency of conversion. Desirably, the synthesis gas input to the methanol synthesis reactor has a molar ratio of hydrogen ($H_2$) to carbon oxides (CO+$CO_2$) in the range of from about 0.5:1 to about 20:1, preferably in the range of from about 2:1 to about 10:1. In another embodiment, the synthesis gas has a molar ratio of hydrogen ($H_2$) to carbon monoxide (CO) of at least 2:1. Carbon dioxide is optionally present in an amount of not greater than 50% by weight, based on total weight of the synthesis gas.

Desirably, the stoichiometric molar ratio is sufficiently high so as maintain a high yield of methanol, but not so high as to reduce the volume productivity of methanol. Preferably, the synthesis gas fed to the methanol synthesis has a stoichiometric molar ratio (i.e., a molar ratio of $H_2$:(2CO+3$CO_2$)) of from about 1.0:1 to about 2.7: 1, more preferably from about 1.1 to about 2.0, more preferably a stoichiometric molar ratio of from about 1.2:1 to about 1.8:1.

The $CO_2$ content, relative to that of CO, in the synthesis gas should be high enough so as to maintain an appropriately high reaction temperature and to minimize the amount of undesirable by-products such as paraffins. At the same time, the relative $CO_2$ to CO content should not be too high so as to reduce methanol yield. Desirably, the synthesis gas contains $CO_2$ and CO at a ratio of from about 0.5 to about 1.2, preferably from about 0.6 to about 1.0.

In one embodiment, the catalyst used in the methanol synthesis process includes an oxide of at least one element selected from the group consisting of copper, silver, zinc, boron, magnesium, aluminum, vanadium, chromium, manganese, gallium, palladium, osmium and zirconium. Preferably, the catalyst is a copper based catalyst, more preferably in the form of copper oxide.

In another embodiment, the catalyst used in the methanol synthesis process is a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst.

In one embodiment, the methanol synthesis catalyst comprises from about 3 wt % to about 30 wt % zinc oxide, based on total weight of the catalyst. Preferably, the methanol synthesis catalyst comprises from about 4 wt % to about 27 wt % zinc oxide, more preferably from about 5 wt % to about 24 wt % zinc oxide.

In embodiments in which copper oxide and zinc oxide are both present in the methanol synthesis catalyst, the ratio of copper oxide to zinc oxide can vary over a wide range. Preferably in such embodiments, the methanol synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

The methanol synthesis catalyst is made according to conventional processes. Examples of such processes can be found in U.S. Pat. Nos. 6,114,279; 6,054,497; 5,767,039; 5,045,520; 5,254,520; 5,610,202; 4,666,945; 4,455,394; 4,565,803; 5,385,949, with the descriptions of each being fully incorporated herein by reference.

In one embodiment, the synthesis gas formed in the synthesis gas conversion plant is cooled prior to sending to the methanol synthesis reactor. Preferably, the synthesis gas is cooled so as to condense at least a portion of the water vapor formed during the synthesis gas process.

The methanol synthesis process used to manufacture the methanol composition of this invention can be any conventional process. Examples of such processes include batch processes and continuous processes. Continuous processes are preferred. Tubular bed processes and fluidized bed processes are particularly preferred types of continuous processes.

In general, the methanol synthesis process takes place according to the following reactions:

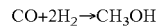

CO+2$H_2$→$CH_3$OH

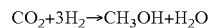

$CO_2$+3$H_2$→$CH_3$OH+$H_2$O

The methanol synthesis process is effective over a wide range of temperatures. In one embodiment, the synthesis gas is contacted with the methanol synthesis catalyst at a temperature in the range of from about 150° C. to about 450° C., preferably in a range of from about 175° C. to about 350° C., more preferably in a range of from about 200° C. to about 300° C.

The process is also operable over a wide range of pressures. In one embodiment, the synthesis gas is contacted with the methanol synthesis catalyst at a pressure in the range of from about 15 atmospheres to about 125 atmospheres, preferably in a range of from about 20 atmospheres to about 100 atmospheres, more preferably in a range of from about 25 atmospheres to about 75 atmospheres.

Gas hourly space velocities vary depending upon the type of continuous process that is used. Desirably, gas hourly space velocity of flow of gas through the catalyst bed is in the range of from about 50 $hr^{-1}$ to about 50,000 $hr^{-1}$. Preferably, gas hourly space velocity of flow of gas through the catalyst bed is in the range of from about 250 $hr^{-1}$ to about 25,000 $hr^{-1}$, more preferably from about 500 $hr^{-1}$ to about 10,000 $hr^{-1}$.

The methanol synthesis process produces a variety of hydrocarbons as by-products. According to the methanol composition of this invention, it is desirable to operate the process so as to maximize not only the amount of methanol formed, but also aldehydes and other alcohols which are particularly desirable in the conversion of oxygenates to olefins. In is particularly appropriate to maximize the amount of methanol formed in the methanol synthesis, and remove hydrocarbons less desirable in the conversion of oxygenates to olefins from the crude methanol product stream formed in the methanol synthesis reactor.

F. Refining Crude Methanol to Make Methanol Product

After reaction, the crude methanol product mixture is further processed to obtain the methanol composition of the invention. Processing is accomplished by any conventional means. Examples of such means include distillation, selective condensation, and selective adsorption. Process conditions, e.g., temperatures and pressures, can vary according to the particular methanol composition desired. It is particularly desirable to minimize the amount of water and light boiling point components in the methanol composition, but without substantially reducing the amount of methanol and desirable aldehydes and/or other desirable alcohols also present.

In one embodiment, the crude methanol product from the methanol synthesis reactor is sent to a let down vessel so as to reduce the pressure to about atmospheric or slightly higher. This let down in pressure allows undesirable light boiling point components to be removed from the methanol composition as a vapor. The vapor is desirably of sufficient quality to use a fuel.

In another embodiment, the crude methanol is sent from the methanol synthesizing unit to a distillation system. The distillation system contains one or more distillation columns which are used to separate the desired methanol composition from water and hydrocarbon by-product streams. Desirably, the methanol composition that is separated from the crude methanol comprises a majority of the methanol and a majority of aldehyde and/or alcohol supplements contained in the crude alcohol prior to separation. Preferably, the methanol composition that is separated from the crude methanol comprises a majority of the acetaldehyde and/or ethanol contained in the crude methanol prior to separation. More preferably, the methanol composition that is separated from the crude methanol is one of the preferred methanol compositions of this invention.

In one embodiment, the distillation system includes a step of treating the methanol steam being distilled so as to remove or neutralize acids in the stream. Preferably, a base is added in the system that is effective in neutralizing organic acids that are found in the methanol stream. Conventional base compounds can be used. Examples of base compounds include alkali metal hydroxide or carbonate compounds, and amine or ammonium hydroxide compounds. In one particular embodiment, about 20 ppm to about 120 ppm w/w of a base composition, calculated as stoichiometrically equivalent NaOH, is added, preferably about 25 ppm to about 100 ppm w/w of a base composition, calculated as stoichiometrically equivalent NaOH, is added.

The invention can include any distillation system that produces a "fusel oil" stream (i.e., a stream having a majority of hydrocarbon compounds with a boiling point greater than that of methanol). It is especially advantageous when the fusel oil stream is liquid taken from a column fed with the crude methanol from the let-down vessel or with the bottoms liquid from a column fed with such crude methanol, the off-take point being at a level below the feed level. Alternatively or additionally, the fusel oil stream is taken from a level above the feed level in such a column. Because some of the higher alcohols are advantageous in the methanol composition of this invention, it is desirable to operate the distillation system to recover the $C_2$–$C_4$ alcohols along with the methanol rather than in the fusel oil stream.

Examples of distillation systems include the use of single and two column distillation columns. Preferably, the single columns operate to remove volatiles in the overhead, methanol product at a high level, fusel oil as vapor above the feed and/or as liquid below the feed, and water as a bottoms stream.

In one embodiment of a two column system, the first column is a "topping column" from which volatiles are taken overhead and methanol liquid as bottoms. The second is a "rectifying column" from which methanol product is taken as an overhead stream or at a high level, and water is removed as a bottoms stream. In this embodiment, the rectifying column includes at least one off-take for fusel oil as vapor above the feed and/or as liquid below the feed.

In another embodiment of a two column system, the first column is a water-extractive column in which there is a water feed introduced at a level above the crude methanol feed level. It is desirable to feed sufficient water to produce a bottoms liquid containing over 40% w/w water, preferably 40% to 60% w/w water, and more preferably 80% to 95% w/w water. This column optionally includes one or more direct fusel oil side off-takes.

In yet another embodiment, the distillation system is one in which an aqueous, semi-crude methanol is taken as liquid above the feed in a single or rectifying column. The semi-crude methanol is passed to a rectifying column, from which methanol product is taken overhead or at a high level. Preferably, water or aqueous methanol is taken as a bottoms stream.

Alternatively, undesirable by-products are removed from the crude methanol stream from the methanol synthesis reactor by adsorption. In such a system, fusel oil can be recovered by regenerating the adsorbent.

IV. Use of the Methanol Composition in the Manufacture of Olefins

The methanol composition of this invention can be used as feed for any conventional process. Examples of such uses include the manufacture of methyl tertiary butyl alcohol (MTBE) for use in reformulated gasolines and oxygenated fuels; the use of methanol as a fuel for fuel cells, use as feedstock to make olefins, and for use in making acetic acid and formaldehyde.

The methanol product stream of this invention is particularly suited for conversion to olefins, particularly ethylene and/or propylene. The methanol product stream can be fed directly to an olefin conversion process or it can be transported in large quantities over great distances and converted to olefins.

According to this invention, the methanol product can be produced in large scale quantities for conversion to olefins, which is of great advantage for further conversion of the olefins to polyolefins such as polyethylene and polypropylene. Advantageously, this invention allows for at least 100,000 metric tons of methanol product per year. Preferably, production is at least 500,000 metric tons per year, more preferably at least 1 million metric tons per year, and most preferably at least 2 million metric tons per year.

In one embodiment, the methanol stream of the invention is separated from a crude methanol stream, and transported to a location geographically distinct from that where the methanol composition was separated from the crude methanol stream. Preferably, the methanol composition of this invention is loaded into a vessel, and the vessel is transported over a body of water to a storage facility. The methanol can be easily transported at least 100, 500 or 1,000 miles or more. Once arriving at the storage facility, the methanol composition is delivered to a storage tank. From the storage tank, the methanol composition is ultimately sent to an olefin conversion unit for conversion to an olefin product. The methanol composition is preferably, loaded onto a ship, with the ship able to contain at least 20,000 tons, preferably at least 40,000 tons, and more preferably at least 80,000 tons.

An advantage of being able to transport the methanol composition is that the units which produce the methanol do not have to be located in close geographic proximity to the olefin conversion unit. This makes it possible to use remote gas reserves. These remote gas reserves would be used as feed for the methanol manufacturing facility. The methanol made at these remote sites can then be easily transported to a suitable location for conversion to olefins. Since olefins and polyolefins (i.e., plastics) demands are typically low at the remote gas sites, there will generally be a desire to transport methanol to high olefins and plastic demand areas. methanol is routinely transported in vessels that are similar to those that transport crude oil and other fuels. Examples of locations of remote gas reserves include the coastline of west Africa, northwest Australia, in the Indian Ocean, and the Arabian Peninsula. Examples of locations of preferred sites to convert methanol to other products such as olefins include the U.S. Gulf coast and northwest Europe.

V. Converting the Methanol Composition to Olefins

A. General Process Description

In one embodiment of the invention, the methanol composition is converted to olefins by contacting the methanol composition with an olefin forming catalyst to form the olefin product. The olefin product is recovered, and water, which forms during the conversion of the oxygenates in the methanol to olefins, is removed. After removing the water, the olefins are separated into individual olefin streams, and each individual olefin stream is available for further processing.

B. Description of Olefin Forming Catalyst

Any catalyst capable of converting oxygenate to olefin can be used in this invention. Molecular sieve catalysts are preferred. Examples of such catalysts include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof, and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B. V., Amsterdam, Netherlands (2001).

The small, medium and large pore molecular sieves have from a 4-ring to a 12-ring or greater framework-type. In a preferred embodiment, the molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZNAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No.4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. No. 4,824, 554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves used in the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

In one embodiment, the molecular sieves used in the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229, −295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve, in a preferred embodiment, is combined with one or more matrix materials. Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 μm to about 0.6 μm with a D90 particle size distribution of less than about 1 μm.

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

C. Adding Other Oxygenates to Methanol Composition

In an optional embodiment of this invention, the methanol composition is converted to olefin along with other oxygenates or diluents. The additional oxygenates or diluents can be co-mixed with the methanol composition or added as a separate feed stream to an oxygenate conversion reactor. In one embodiment, the additional oxygenate is one or more alcohol(s), preferably aliphatic alcohol(s) where the aliphatic moiety of the alcohol(s) has from 1 to 10 carbon atoms, preferably from 1 to 5 carbon atoms, and most preferably from 1 to 4 carbon atoms. Ethanol is most preferred. The alcohols include lower straight and branched chain aliphatic alcohols and their unsaturated counterparts. Non-limiting examples of oxygenates include ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The methanol feed stream, in one embodiment, contains one or more diluent(s), typically used to reduce the concentration of the methanol, and are generally non-reactive to the oxygenates in the composition or to the molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent is either added directly to the methanol feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50 more percent, most preferably from about 5 to about 25 mole percent. In one embodiment, other hydrocarbons are added to the feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

D. General Conditions for Converting Methanol to Olefins

According to the reaction process of this invention, oxygenate is contacted with olefin forming catalyst to form an olefin product, particularly ethylene and propylene. The process for converting the oxygenate feedstock is, preferably, a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described-in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

One preferred reactor type is a riser reactor. These types of reactors are generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one embodiment of the invention, a fluidized bed process or high velocity fluidized bed process includes a reactor system, catalyst separation system, and a regeneration system. The reactor system preferably is a fluid bed reactor system. In one embodiment, the fluid bed reactor system has a first reaction zone within one or more riser reactors, and a second reaction zone within at least one catalyst separation vessel, preferably comprising one or more cyclones. In one embodiment, one or more riser reactors and catalyst separation vessel is contained within a single reactor vessel.

An oxygenate stream, preferably containing one or more oxygenates, and optionally one or more diluents, is fed to a fluid bed reactor in which a molecular sieve catalyst composition is introduced. In one embodiment, the molecular sieve catalyst composition is contacted with a liquid or gas, or combination thereof, prior to being introduced to the riser reactor. Preferably, the liquid is water or methanol, and the gas is an inert gas such as nitrogen.

In one embodiment of the invention, the temperature of the regenerator is indirectly controlled by controlling the amount of heat generated in the reactor. One example of controlling the amount of heat generated is by introducing at least a portion of the oxygenate stream into the reactor in liquid form. The greater the liquid content, the less heat generated, since the exothermic heat of reaction of oxygenate conversion is partially absorbed by the endothermic heat of vaporization of the liquid portion of the feed.

In another embodiment, the amount of oxygenate stream that is fed to a reactor system in liquid form is from about 0.1 weight percent to about 85 weight percent, based on the total weight of the oxygenate stream, including any diluent contained therein. Preferably the amount of the oxygenate stream that is fed to the reactor system in liquid form is from about 1 weight percent to about 75 weight percent, more preferably from about 5 weight percent to about 65 weight percent, based on the total weight of the oxygenate stream, including any diluent contained therein.

The liquid and vapor portion of the feed may be the same composition, or may contain varying proportions of the same or different oxygenates and same or different diluents. One particularly effective liquid diluent is water, due to its relatively high heat of vaporization. Other useful diluents are described above. Proper selection of the temperature and pressure of any appropriate oxygenate and/or diluent being fed to the reactor will ensure at least a portion is in the liquid phase as it enters the reactor and/or comes into contact with the catalyst or a vapor portion of the feed and/or diluent.

Optionally, the liquid fraction of the oxygenate stream is split into portions and introduced into the reactor at a multiplicity of locations along its length. This can be done with the oxygenate feed, the diluent, or both. Preferably, this is done with the diluent portion of the feed. Another option is to provide a nozzle which introduces the total liquid fraction of the feed into the inlet zone or reactor in a manner such that the nozzle forms liquid droplets of an appropriate size distribution which, when entrained with the gas and solids introduced to the inlet zone or reactor, vaporize gradually along the length of the reactor. Either of these arrangements or a combination thereof may be used to better control the amount of heat generated. The means of introducing a multiplicity of liquid feed points in a reactor or designing a liquid feed nozzle to control droplet size distribution is well known in the art and is not discussed here.

In another embodiment of the invention, the temperature of the regenerator is controlled by circulating heat absorbing solid particles between the reactor and regenerator. The heat absorbing solid particles are substantially inert solid materials, which do not substantially adversely affect the conversion of the oxygenate to olefin. Preferably, the heat absorbing solid particles contain no molecular sieve as a part of the solid particles. However, the heat absorbing solid particles are, preferably, circulated along with the molecular sieve catalyst between the reactor and the regenerator. Suitable materials for use as heat absorbing solid particles include such materials as metals, metal oxides, and mixtures thereof. Particularly suitable materials are those used as matrices for molecular sieve catalyst formulation, e.g., fillers and binders such as silicas and aluminas, among others, and mixtures thereof. Desirably, the heat absorbing solid particles have a heat capacity of from about 0.8 cal/g-° C., and most preferably from about 0.1 to about 0.5 cal/g-° C. In another embodiment, the heat absorbing solids is present at a solids to catalyst ratio of from about 0.01–10:1, more preferably from about 0.05–5:1.

In an embodiment where catalyst and heat absorbing solid particles are circulated between the reactor and regenerator, the catalyst and heat absorbing solid particles are optionally circulated at a rate that is from about 1 to about 200 times that of the total rate of the oxygenate stream input to the reactor. Preferably, the catalyst and heat absorbing solid particles are circulated at a rate that is from about 5 to about 160 times that of the total rate of the oxygenate stream input to the reactor; more preferably from about 10 to about 100 times that of the total rate of the oxygenate stream input to the reactor.

In another embodiment, the molecular sieve catalyst itself is circulated between the reactor and regenerator at a rate of from about 1 to about 100 times that of the total rate of the oxygenate stream input to the reactor. Preferably, the molecular sieve catalyst is circulated at a rate that is from about 5 to about 80 times that of the total rate of the oxygenate stream input to the reactor; more preferably from about 10 to about 50 times that of the total rate of the oxygenate stream input to the reactor.

The oxygenate in the oxygenate feed stream entering the reactor system is preferably converted, partially or fully, in a reactor zone forming an olefin product and a coked catalyst. The olefin product and coked catalyst, as well as any unconverted or unreacted oxygenate, are sent to a catalyst separation vessel where the coked catalyst is separated from the olefin product and the unconverted or unreacted oxygenate.

In a preferred embodiment, cyclones within the separation vessel are used to separate the coked catalyst composition. Gravity effects within the disengaging vessel can also be effective in separating the catalyst. Other processss for separating the catalyst from the gaseous effluent include the use of plates, caps, elbows, and the like.

The average reaction temperature employed in the conversion process, specifically within the reactor, is of from about 250° C. to about 800° C. Preferably the average reaction temperature within the reactor is from about 250° C. to about 750° C.; more preferably, from about 300° C. to about 650° C.; yet more preferably from about 350° C. to about 600° C.; and most preferably from about 400° C. to about 500° C.

The pressure employed in the conversion process, specifically within the reactor, is not critical. The reaction pressure is based on the partial pressure of the feedstock exclusive of any diluent therein. Typically the reaction pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor is preferably sufficient to fluidize the molecular sieve catalyst composition within a reaction zone of the reactor. The SGV in the process, particularly within the reactor system, more particularly within a riser reactor, is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec.

According to one embodiment, the conversion of oxygenate, particularly the conversion of methanol, is from 90 wt % to 98 wt %. According to another embodiment the conversion of methanol is from 92 wt % to 98 wt %, preferably from 94 wt % to 98 wt %.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt %; preferably from 98.2 wt % to 99 wt %.

It is desirable to maintain an amount of coke on the catalyst in the reaction vessel to enhance the formation of desired olefin product, particularly ethylene and propylene. It is particularly desirable that the catalyst in the reactor be maintained to contain at least about 1.5 wt % coke. Preferably, the amount of coke maintained on the catalyst in the reactor should be from about 2 wt % to about 30 wt %.

VI. Olefin Production Revcovery and Use

In one embodiment, olefin product and other gases are withdrawn from the reactor and are passed through a recovery system. Any conventional recovery system, technique and/or sequence useful in separating olefin(s) and purifying olefin(s) from other gaseous components can be used in this invention. Examples of recovery systems include one or more or a combination of various separation, fractionation and/or distillation towers, columns, and splitters, and other associated equipment; for example, various condensers, heat exchangers, refrigeration systems or chill trains, compressors, knock-out drums or pots, pumps, and the like.

Non-limiting examples of distillation towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene ($C_2$) splitter, propylene ($C_3$) splitter, butene ($C_4$) splitter, and the like.

Various recovery systems useful for recovering predominately olefin(s), preferably prime or light olefin(s) such as ethylene, propylene and/or butene are described in U.S. Pat. No. 5,960,643, U.S. Pat. Nos. 5,019,143, 5,452,581 and 5,082,481, U.S. Pat. No. 5,672,197, U.S. Pat. No. 6,069,288, U.S. Pat. No. 5,904,880, U.S. Pat. No. 5,927,063, and U.S. Pat. No. 6,121,504, U.S. Pat. No. 6,121,503, and U.S. Pat. No. 6,293,998, which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428, U.S. Pat. No. 6,293,999, and U.S. patent application Ser. No. 09/689,363 filed Oct. 20, 2000, which are herein incorporated by reference.

The ethylene and propylene streams produced and recovered according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives may be formed from the ethylene, propylene and $C_4+$ olefins, particularly butylene, separated according to this invention. The olefins separated according to this invention can also be used in the manufacture of such compounds as aldehydes, acids such as $C_2$–$C_{13}$ mono carboxylic acids, alcohols such as $C_2$–$C_{12}$ mono alcohols, esters made from the $C_2$–$C_{12}$ mono carboxylic acids and the $C_2$–$C_{12}$ mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4+$ olefins, butylene in particular, are particularly suited for the manufacture of aldehydes, acids, alcohols, esters made from $C_5$–$C_{13}$ mono carboxylic acids and $C_5$–$C_{13}$ mono alcohols and linear alpha olefins.

VII. Examples of the Invention

EXAMPLE 1

SAPO-34 molecular sieve catalyst was used to evaluate the conversion of certain alcohols to olefins. Experiments were performed with the use of a microflow reactor. Typically, 95 mg of formulated catalyst or 38 mg of sieve was mixed with 1 g of 100-μm silicon carbide. The mixture was loaded into the reactor, which is made of ¼" silicon steel tubing. The reactor temperature was increased to 475° C. while the catalyst was under He flow (46 ml/min), and waited for ca. 30 to 40 min for the temperature to stabilize. Methanol was used as the feedstock, and was flowed through reactor at ca. 80 μl/min at 475 C, 25 psig and 100 WHSV. The reactor effluent was sampled in a multi-loop sampling valve to obtain the gas phase selectivity data. The collected effluent samples were analyzed by on-line gas chromatography (Hewlett Packard 6890) equipped with a flame ionization detector. The chromatographic column used was a Q-column.

The weighed average yields were calculated based on the following formula:

$$x_1*y_1+(x_2-x_1)*y_2+(x_3-x_2)*(y_2+y_3)/2+(x_4-x_3)*(y_3+y_4)/2+\ldots,$$

where $x_i$ and $y_i$ are yield and g methanol fed/g sieve, respectively. Note that WHSV was reported based on the weight of the sieve. Methanol converted at less than ca. 10% conversions was not counted in the calculations. Selectivities were calculated by normalizing the yield data excluding methanol, DME, methyl ethyl ether, ethyl ether and the added component, e.g., ethanol and acetaldehyde. The result is shown in Table 1.

EXAMPLE 2

The procedure of Example 1 was repeated, except that a mixture of 2.5 wt % ethanol and 97.5 wt % methanol was used as the feedstock. The result is shown in Table 1.

TABLE 1

| Feed | $C_1$ (wt %) | $C_2$= (wt %) | $C_2$o (wt %) | $C_3$= (wt %) | $C_3$o (wt %) | $C_4$ (wt %) | $C_5$+(wt %) | $C_{2+3}$= (wt %) |
|---|---|---|---|---|---|---|---|---|
| 100 wt % methanol | 1.83 | 36.53 | 0.29 | 40.72 | 0.57 | 13.71 | 6.36 | 77.25 |
| 2.5 wt % ethanol + 97.5 wt % methanol | 1.47 | 38.38 | 0.26 | 39.79 | 0.48 | 13.71 | 5.91 | 78.17 |

Table 1 shows that ethylene yield is improved with the addition of ethanol to the methanol feedstock.

EXAMPLE 3

Example 1 was repeated, including running methanol feedstocks having added thereto acetaldehyde (ethanal), acetone and butanone. A LOWOX column was used in the analysis of the products. The results are shown in Table 2.

TABLE 2

| Feed | $C_1$ (wt %) | $C_2$= (wt %) | $C_2$o (wt %) | $C_3$= (wt %) | $C_3$o (wt %) | $C_4$ (wt %) | Oxys (wt %) | $C_{2+3}$= (wt %) |
|---|---|---|---|---|---|---|---|---|
| 100 wt % methanol | 1.82 | 36.27 | 0.29 | 41.11 | 0.58 | 19.12 | 0.83 | 77.37 |
| 5 wt % ethanal + 95 wt % methanol | 1.88 | 37.49 | 0.30 | 35.84 | 0.50 | 16.97 | 7.03 | 73.33 |
| 5 wt % acetone + 95 wt % methanol | 1.71 | 34.22 | 0.27 | 39.61 | 0.55 | 17.08 | 6.55 | 73.83 |
| 5 wt % butanone + 95 wt % methanol | 1.61 | 32.10 | 0.25 | 34.36 | 0.48 | 22.30 | 8.90 | 66.45 |

Note that the terms $C_1$, $C_2$=, $C_2$°, $C_3$=, $C_3$o, $C_4$, $C_5$+, $C_{2+3}$=, $C_{4+}$ and oxys, as denoted in Table 1 and/or Table 2 refer, respectively, to methane, ethylene, ethane, propylene, propane, butenes and butanes, hydrocarbons that contain five or more than five carbons, ethylene and propylene, and oxygen-containing hydrocarbons present except for methanol and dimethyl ether (DME). Table 2 indicates that the addition of aldehyde reduces $C_4$ make, and that the addition of the ketones reduces methane formation.

Having now fully described this invention, it will be appreciated by those skilled in the art that the invention can be performed within a wide range of parameters within what is claimed, without departing from the spirit and scope of the invention.

The invention claimed is:

1. A process for forming an olefin stream, the process comprising the steps of:
   a) contacting a synthesis gas stream with a methanol synthesis catalyst to form a crude methanol stream containing methanol, ethanol and acetaldehyde;
   b) separating a methanol composition from the crude methanol stream, wherein the methanol composition comprises a majority of the methanol and a majority of the acetaldehyde contained in the oxygenate containing stream; and
   c) contacting the methanol composition with an olefin forming catalyst to form an olefin stream.

2. The process of claim 1, wherein the synthesis gas stream is made by contacting a carbon containing compound with water or oxygen.

3. The process of claim 2, wherein the carbon containing compound is selected from the group consisting of biomass, natural gas, $C_1$ to $C_5$ hydrocarbons, naphtha, heavy petroleum coils, coke, and mixtures thereof.

4. The process of claim 1, wherein the methanol composition is separated by distillation.

5. The process of claim 1, wherein the methanol composition separated in step b) comprises:
   i. at least 50 wt % and less than 99.85 wt % methanol, based on total weight of the methanol composition;
   ii. greater than 10 wppm and not greater than 15 wt % ethanol, based on total weight of the methanol composition; and
   iii. greater than 10 wppm, and not greater than 15 wt % acetaldehyde, based on total weight of the methanol composition.

6. The process of claim 5, wherein the methanol composition comprises at least 75 wt % methanol, based on total weight of the methanol composition.

7. The process of claim 6, wherein the methanol composition comprises at least 80 wt % methanol, based on total weight of the methanol composition.

8. The process of claim 7, wherein the methanol composition comprises at least 85 wt % methanol based on total weight of the methanol composition.

9. The process of claim 8, wherein the methanol composition comprises at least 90 wt % methanol, based on total weight of the methanol composition.

10. The process of claim 5, wherein the methanol composition comprises not greater than 99 wt % methanol, based on total weight of the methanol composition.

11. The process of claim 10, wherein the methanol composition comprises not greater than 98 wt % methanol, based on total weight of the methanol composition.

12. The process of claim 11, wherein the methanol composition comprises not greater than 97 wt % methanol, based on total weight of the methanol composition.

13. The process of claim 12, wherein the methanol composition comprises not greater than 96 wt % methanol, based on total weight of the methanol composition.

14. The process of claim 5, wherein the methanol composition comprises at least 100 wppm ethanol, based on total weight of the methanol composition.

15. The process of claim 14, wherein the methanol composition comprises at least 1,000 wppm ethanol, based on total weight of the methanol composition.

16. The process of claim 15, wherein the methanol composition comprises at least 10,000 wppm ethanol, based on total weight of the methanol composition.

17. The process of claim 16, wherein the methanol composition comprises at least 0.1 wt % ethanol, based on total weight of the methanol composition.

18. The process of claim 5, wherein the methanol composition comprises not greater than 12 wt % ethanol, based on total weight of the methanol composition.

19. The process of claim 18, wherein the methanol composition comprises not greater than 10 wt % ethanol, based on total weight of the methanol composition.

20. The process of claim 19, wherein the methanol composition comprises not greater than 8 wt % ethanol, based on total weight of the methanol composition.

21. The process of claim 5, wherein the methanol composition comprises at least 100 wppm acetaldehyde, based on total weight of the methanol composition.

22. The process of claim 21, wherein the methanol composition comprises at least 1,000 wppm acetaldehyde, based on total weight of the methanol composition.

23. The process of claim 22, wherein the methanol composition comprises at least 10,000 wppm acetaldehyde, based on total weight of the methanol composition.

24. The process of claim 23, wherein the methanol composition comprises at least 0.1 wt % anetaldehyde, based on total weight of the methanol composition.

25. The process of claim 24, wherein the methanol composition comprises not greater than 12 wt % acetaldehyde, based on total weight of the methanol composition.

26. The process of claim 25, wherein the methanol composition comprises not greater than 10 wt % acetaldehyde, based on total weight of the methanol composition.

27. The process of claim 26, wherein the methanol composition comprises not greater than 8 wt % acetaldehyde, based on total weight of the methanol composition.

28. The process of claim 1, wherein the methanol composition further comprises ketone at less than 50% that of the acetaldehyde.

29. The process of claim 28, wherein the methanol composition further comprises ketone at less than 60% that of the acetaldehyde.

30. The process of claim 29, wherein the methanol composition further comprises ketone at less than 70% that of the acetaldehyde.

31. The process of claim 1, wherein the methanol composition further comprises at least 0.1 wt % and not greater than 12 wt % water, based on total weight of the methanol composition.

32. The process of claim 31, wherein the methanol composition further comprises at least 0.5 wt % water, based on total weight of the methanol composition.

33. The process of claim 32, wherein the methanol composition further comprises at least 1.0 wt % water, based on total weight of the methanol composition.

34. The process of claim 33, wherein the methanol composition further comprises at least 1.5 wt % water, based on total weight of the methanol composition.

35. The process of claim 34, wherein the methanol composition further comprises not greater than 10 wt % water, based on total weight of the methanol composition.

36. The process of claim 35, wherein the methanol composition further comprises not greater than 8 wt % water, based on total weight of the methanol composition.

37. The process of claim 36, wherein the methanol composition further comprises not greater than 5 wt % water, based on total weight of the methanol composition.

38. The process of claim 1, further comprising the step of transporting the methanol composition separated in step b) to a location geographically distinct from that where the methanol composition was separated from the oxygenate stream.

39. The process of claim 38, wherein the methanol composition is separated at a remote natural gas location, shipped across a body of water, and the methanol composition is contacted with the olefin forming catalyst at a location integrated with a polyolefin manufacturing plant.

40. The process of claim 1, wherein the olefin forming catalyst is a molecular sieve catalyst.

41. The process of claim 40, wherein the molecular sieve catalyst is a silicoaluminophosphate molecular sieve.

42. The process of claim 41, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, and metal containing molecular sieves thereof.

43. The process of claim 42, wherein the silicoaluminophosphate molecular sieve is selected from the group consisting of SAPO-18, SAPO-34, SAPO-35, SAPO-44, SAPO-56, ALPO-18, ALPO-34, and metal containing molecular sieves thereof.

44. The process of claim 43, wherein the silicoaluminophosphate molecular sieve is selected from the group consisting of SAPO-18, SAPO-34, ALPO-34, ALPO-18, and metal containing molecular sieves thereof.

45. The process of claim 1, wherein the olefin stream formed in step c) is contacted with a polyolefin forming catalyst to form a polyolefin.

46. A process for forming an olefin stream, the process comprising the steps of:
a) providing a crude methanol stream;
b) separating a methanol composition from the crude methanol stream, wherein the separated methanol composition contains less than 99.85 wt % methanol and greater than 10 wppm acetaldehyde, based on total weight of the methanol stream; and
b) contacting the methanol composition with an olefin forming catalyst to form an olefin stream.

47. The process of claim 46, wherein the methanol composition comprises at least 50 wt % methanol, based on total weight of the methanol composition.

48. The process of claim 47, wherein the methanol composition comprises at least 75 wt % methanol, based on total weight of the methanol composition.

49. The process of claim 48, wherein the methanol composition comprises at least 80 wt % methanol, based on total weight of the methanol composition.

50. The process of claim 49, wherein the methanol composition comprises at least 85 wt % methanol, based on total weight of the methanol coniposition.

51. The process of claim 50, wherein the methanol composition comprises at least 90 wt % methanol, based on total weight of the methanol composition.

52. The process of claim 46, wherein the methanol composition comprises not greater than 99 wt % methanol, based on total weight of the methanol composition.

53. The process of claim 52, wherein the methanol composition comprises not greater than 98 wt % methanol, based on total weight of the methanol composition.

54. The process of claim 53, wherein the methanol composition comprises not greater than 97 wt % methanol, based on total weight of the methanol composition.

55. The process of claim 54, wherein the methanol composition comprises not greater than 96 wt % methanol, based on total weight of the methanol composition.

56. The process of claim 46, wherein the methanol composition comprises at least 100 wppm acetaldehyde, based on total weight of the methanol composition.

57. The process of claim 56, wherein the methanol composition comprises at least 1,000 wppm acetaldehyde, based on total weight of the methanol composition.

58. The process of claim 57, wherein the methanol composition comprises at least 10,000 wppm acetaldehyde, based on total weight of the methanol composition.

59. The process of claim 58, wherein the methanol composition comprises at least 0.1 wt % acetaldehyde, based on total weight of the methanol composition.

60. The process of claim 46, wherein the methanol composition comprises not greater than 15 wt % acetaldehyde, based on total weight of the methanol composition.

61. The process of claim 60, wherein the methanol composition comprises not greater than 12 wt % acetaldehyde, based on total weight of the methanol composition.

62. The process of claim 61, wherein the methanol composition comprises not greater than 10 wt % acetaldohyde, based on total weight of the methanol composition.

63. The process of claim 62, wherein the methanol composition coniprises not greater than 8 wt % acetaldehyde, based on total weight of the methanol composition.

64. The process of claim 46, wherein the methanol composition further comprises ketone at less than 50% that of the acetaldehyde.

65. The process of claim 64, wherein the methanol composition further comprises ketone at less than 60% that of the acetaldehyde.

66. The process of claim 65, wherein the methanol composition further comprises ketone at less than 70% that of the acetaldehyde.

67. The process of claim 46, wherein the methanol composition further comprises at least 0.1 wt % and not greater than 12 wt % water, based on total weight of the methanol composition.

68. The process of claim 67, wherein the methanol composition further comprises at least 0.5 wt % water, based on total weight of the methanol composition.

69. The process of claim 68, wherein the methanol composition further comprises at least 1.0 wt % water, based on total weight of the methanol composition.

70. The process of claim 69, wherein the methanol composition further comprises at least 1.5 wt % water, based on total weight of the methanol composition.

71. The process of claim 46, wherein the methanol composition further comprises not greater than 10 wt % water, based on total weight of the methanol composition.

72. The process of claim 71, wherein the methanol composition further comprises not greater than 8 wt % water, based on total weight of the methanol composition.

73. The process of claim 72, wherein the methanol composition further comprises not greater than 5 wt % water, based on total weight of the methanol composition.

74. The process of claim 46, further comprising the step of transporting the methanol composition separated in step b) to a location geographically distinct from that where the methanol composition was separated from the oxygenate stream.

75. The process of claim 74, wherein the methanol composition is separated at a remote natural gas location, shipped across a body of water, and the methanol composition is contacted wit the olefin forming catalyst at a location integrated with a palyolefin manufacturing plant.

76. The process of claim 46, wherein the olefin forming catalyst is a molecular sieve catalyst.

77. The process of claim 76, wherein the molecular sieve catalyst is a silicoaluminophosphate molecular sieve.

78. The process of claim 77, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, and metal containing molecular sieves thereof.

79. The process of claim 78, wherein the silicoaluminophosphate molecular sieve is selected from the group consisting of SAPO-18, SAPO-34, SAPO-35, SAPO-44, SAPO-56, ALPO-18, ALPO-34, and metal containing molecular sieves thereof.

80. The process of claim 79, wherein the silicoaluminophosphate molecular sieve is selected from the group consisting of SAPO-18, SAPO-34, ALPO-34, ALPO-18, and metal containing molecular sieves thereof.

81. The process of claim 46, wherein the olefin steam formed in step c) is contacted with a polyolefin forming catalyst to form a polyolefin.

82. A process for forming an olefin stream, the process comprising the steps of:
  a) contacting a synthesis gas stream with a methanol synthesis catalyst to form a crude methanol stream containing methanol, ethanol and acetaldehyde;
  b) separating a methanol composition from the crude methanol stream, wherein the methanol composition comprises a majority of the methanol and a majority of the acetaldehyde contained in the crude methanol stream;
  c) transporting the methanol composition to a location geographically distinct from that where the methanol composition was separated from the crude methanol stream; and
  d) contacting the methanol composition with an olefin forming catalyst to form an olefin stream.

83. The process of claim 82, wherein the methanol composition is separated at a remote natural gas location in step b), and transported in step c) by shipping across a body of water, and contaeted with the olefin forming catalyst in step d) at a location integrated with a polyolefin manufacturing plant.

84. The process of claim 82, wherein the olefin forming catalyst is a molecular sieve catalyst.

85. The process of claim 84, wherein the molecular sieve catalyst is a silicoaluminophosphate molecular sieve.

86. The process of claim 85, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAFO-56, ALPO-5, ALPO-l 1, ALPO-11, ALPO-31, ALPO-34, ALPO-36, ALPO-37, ALPO-46, and metal containing molecular sieves thereof.

87. The process of claim 86, wherein the silicoaluminophosphate molecular sieve is selected from the group consisting of SAPO-18, SAPO-34, SAPO-35, SAPO-44, SAPO-56, ALPO-18, ALPO-34, and metal containing molecular sieves thereof.

88. The process of claim 87, wherein the silicoaluminophosphate molecular sieve is selected from the group consisting of SAPO-18, SAPO-34, SAPO34, SAPO-44, ALPO-18, and metal containing molecular sieves thereof.

89. The process of claim 82, wherein the olefin stream formed in step d) is contacted with a polyolfin forming catalyst to form a polyolefin.

90. A process for forming an olefin stream, the process comprising the steps of:
  a) contacting a synthesis gas stream with a methanol synthesis catalyst to form a crude methanol stream containing methanol, ethanol and acetaldehyde;
  b) separating a methanol composition from the crude methanol stream, wherein the methanol composition comprises:
    i. at least 50 wt % and less than 99.85 wt % methanol based on total weight of the methanol composition;
    ii. greater than 10 wppm alcohol supplement that includes at least one alcohol selected from the group consisting of ethanol, propanol and butanol, based on total weight of the methanol composition;
    iii. greater than 10 wppm alciehyde supplements based on total weight of the methanol composition;

c) transporting the methanol composition to a location geographically distinct from that where the methanol composition was separated from the crude methanol stream; and d) contacting the methanol composition with an olefin forming catalyst to form an olefin stream.

91. The process of claim 90, wherein the methanol composition is separated at a remote natural gas location in step b), and transported in step c) by shipping across a body of water, and contacted with the olefin forming catalyst in step d) at a location integrated with a polyolefin manufacturing plant.

92. The process of claim 90, wherein the olefin forming catalyst is a molecular sieve catalyst.

93. The process of claim 92, wherein the molecular sieve catalyst is a silicoaluminophosphate molecular sieve.

94. The process of claim 93, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, ALPO-5, ALPO-11, ALPO-18, ALPO-31, ALPO-34, ALPO-36, ALPO-37, ALPO-46, and metal containing molecular sieves thereof.

95. The process of claim 94, wherein the silicoaluminophosphate molecular sieve is selected from the group consisting of SAPO-18, SAPO-34, SAPO-35, SAPO-44, SAPO-56, ALPO-18, ALPO-34, and metal containing molecular sieves thereof.

96. The process of claim 95, wherein the silicoaluminophosphate molecular sieve is selected from the group consisting of SAPO-18, SAPO-34, ALPO-34, ALPO-18, and metal containing molecular sieves thereof.

97. The process of claim 90, wherein the olefin stream formed in step d) is contacted with a polyolefin forming catalyst to form a polyolefin.

98. The process of claim 90, wherein the methanol composition comprises at least 75 wt % methanol, based on total weight of the methanol composition.

99. The process of claim 98, wherein the methanol composition comprises at least 80 wt % methanol, based on total weight of the methanol composition.

100. The process of claim 99, wherein the methanol composition comprises at least 85 wt % methanol, based on total weight of the methanol composition.

101. The process of claim 100, wherein the methanol composition comprises at least 90 wt % methanol, based on total weight of the methanol composition.

102. The process of claim 90, wherein the methanol composition comprises not greater than 99 wt % methanol, based on total weight of the methanol composition.

103. The process of claim 102, wherein the methanol composition comprises not greater than 98 wt % methanol, based on total weight of the methanol composition.

104. The process of claim 103, wherein the methanol composition comprises not greater than 97 wt % methanol, based on total weight of the methanol composition.

105. The process of claim 104, wherein the methanol composition comprises not greater than 96 wt % methanol, based on total weight of the methanol composition.

106. The process of claim 90, wherein the methanol composition comprises at least 100 wppm alcohol supplement based on total weight of the methanol composition.

107. The process of claim 106, wherein the methanol composition comprises at least 1,000 wppm alcohol supplement, based on total weight of the methanol composition.

108. The process of claim 107, wherein the methanol composition comprises at least 10,000 wppm alcohol supplement, based on total weight of the methanol composition.

109. The process of claim 108, wherein the methanol composition comprises at least 0.1 wt % alcohol supplement, based on total weight of the methanol composition.

110. The process of claim 90, wherein the methanol composition comprises not greater than 15 wt % alcohol supplement, based on total weight of the methanol composition.

111. The process of claim 110, wherein the methanol composition comprises not greater than 12 wt % alcohol supplement, based on total weight of the methanol composition.

112. The process of claim 111, wherein the methanol composition comprises not greater than 10 wt % alcohol supplement, based on total weight of the methanol composition.

113. The process of claim 112, wherein the methanol composition comprises not greater than 8 wt % alcohol supplement, based on total weight of the methanol composition.

114. The process of claim 90, wherein the methanol composition comprises at least 100 wppm aldehyde supplement, based on total weight of the methanol composition.

115. The process of claim 114, wherein the methanol composition comprises at least 1,000 wppm aldehyde supplement, based on total weight of the methanol composition.

116. The process of claim 115, wherein the methanol composition comprises at least 10,000 wpprn aldehyde supplement, based on total weight of the methanol composition.

117. The process of claim 116, wherein the methanol composition comprises at least 0.1 wt % aldehyde supplement, based on total weight of the methanol composition.

118. The process of claim 90, wherein the methanol composition comprises not greater than 15 wt % aldehyde supplement, based on total weight of the methanol composition.

119. The process of claim 118, wherein the methanol composition comprises not greater than 12 wt % aldehyde supplement, based on total weight of the methanol composition.

120. The process of claim 119, wherein the methanol composition comprises not greater than 10 wt % aldehyde supplement, based on total weight of the methanol composition.

121. The process of claim 120, wherein the methanol composition comprises not greater than 8 wt % aldehyde supplement, based on total weight of the methanol composition.

122. The process of claim 90, wherein the alcohol supplement includes ethanol.

123. The process of claim 90, wherein the aldehyde supplement is at least one aldehyde selected from the group consisting of formaldehyde, acetaldehyde, proprionaldehyde, butyraldehyde, and valeraldehyde.

124. The process of claim 123, wherein the aldehyde supplement is acetaldehyde.

125. The process of claim 90, wherein the methanol composition further comprises ketone at less than 50% that of the alcohol supplement or the aldehyde supplement.

126. The process of claim 125, wherein the methanol composition further comprises ketone at less than 60% that of the alcohol supplement or the aldehyde supplement.

127. The process of claim 126, wherein the methanol composition further comprises ketone at less than 70% that of the alcohol supplement or the aldehyde supplement.

128. The process of claim 90, wherein the methanol composition further comprises at least 0.1 wt % and not greater than 12 wt % water, based on total weight of the methanol composition.

129. The process of claim 128, wherein the methanol composition further comprises at least 0.5 wt % water, based on total weight of the methanol composition.

130. The process of claim 129, wherein the methanol composition further comprises at least 1.0 wt % water, based on total weight of the methanol composition.

131. The process of claim 130, wherein the methanol composition further comprises at least 1.5 wt % water, based on total weight of the methanol composition.

132. The process of claim 128, wherein the methanol composition further comprises not greater than 10 wt % water, based on total weight of the methanol composition.

133. The process of claim 132, wherein the methanol composition further comprises not greater than 8 wt % water, based on total weight of the methanol composition.

134. The process of claim 133, wherein the methanol composition further comprises not greater than 5 wt % water, based on total weight of the methanol composition.

* * * * *